United States Patent [19]

Slater et al.

[11] Patent Number: 5,392,789
[45] Date of Patent: Feb. 28, 1995

[54] ENDOSCOPIC SCISSORS HAVING SCISSOR ELEMENTS LOOSELY ENGAGED WITH A CLEVIS

[75] Inventors: Charles R. Slater, Fort Lauderdale; Jurgen A. Kortenbach, Miami Springs; John Starkey, Pembrooke Pines, all of Fla.

[73] Assignee: Symbiosis Corporation, Miami, Fla.

[21] Appl. No.: 140,260

[22] Filed: Oct. 21, 1993

Related U.S. Application Data

[63] Continuation-in-part of Ser. No. 922,023, Jul. 28, 1992, Pat. No. 5,331,971, which is a continuation of Ser. No. 680,392, Apr. 4, 1991, Pat. No. 5,192,298.

[51] Int. Cl.⁶ ............................................. A61B 10/00
[52] U.S. Cl. ..................................... 128/751; 606/205
[58] Field of Search ............................... 128/749, 751; 606/205-208; 403/301, 302-304

[56] References Cited

U.S. PATENT DOCUMENTS

| | | | |
|---|---|---|---|
| 2,216,344 | 10/1940 | Hampton | 403/301 X |
| 2,507,881 | 5/1950 | Bennett | 403/301 |
| 4,887,613 | 12/1989 | Esser et al. | 128/751 |
| 4,944,093 | 7/1990 | Falk | 606/205 X |
| 5,067,843 | 11/1991 | Nova | 403/301 |
| 5,201,759 | 4/1993 | Ferzli | 128/751 X |

*Primary Examiner*—Lee S. Cohen
*Assistant Examiner*—Samuel Gilbert
*Attorney, Agent, or Firm*—David P. Gordon

[57] ABSTRACT

An endoscopic scissors includes a clevis having a relatively large diameter bore in its first arm and relatively smaller diameter bore in its second arm. A pair of scissor elements having mounting/pivot holes are mounted between the clevis arms. Either the small diameter bore in the second clevis arm or the mounting/pivot hole in the scissor element closest to the second clevis arm is threaded. A stepped diameter axle pin having a threaded portion is inserted with its smaller end entering the larger diameter bore of the first clevis arm. The threaded portion of the axle pin threadably engages either the threaded bore in the second clevis arm or the threaded mounting/pivot hole of the scissor element closest to the second clevis arm. In one embodiment, the bore in the second clevis arm is not threaded and the threaded portion of the axle pin engages only the threaded threaded mounting/pivot hole of the scissor element closest to the second clevis arm. Both ends of the axle pin float in respective clevis arm bores. In another embodiment where the scissor element closest to the second clevis arm is kept stationary, the threaded portion of the axle pin engages the threaded bore in the second clevis arm. The larger end of the axle pin floats in the large diameter bore of the first clevis arm. In a third embodiment, a washer is placed between the second clevis arm and the scissor element closest to it and the axle pin engages the threaded bore in the second clevis arm.

17 Claims, 4 Drawing Sheets

ENDOSCOPIC SCISSORS HAVING SCISSOR ELEMENTS LOOSELY ENGAGED WITH A CLEVIS

This application is a continuation-in-part of application Ser. No. 07/922,023, filed Jul. 28, 1992, now U.S. Pat. No. 5,331,971, which is a continuation of Ser. No. 07/680,392, filed Apr. 4, 1991, which has issued as U.S. Pat. No. 5,192,298, which is hereby incorporated by reference in its entirety herein. This application is also related to co-owned U.S. Pat. No. 5,152,778 for "Clevis for Disposable Laparoscopic Instrument", U.S. Pat. No. 5,171,256 for "Single Acting Disposable Laparoscopic Scissors", and U.S. Pat. No. 5,203,785 for "Laparoscopic Hook Scissors", all of which are hereby incorporated by reference herein in their entireties.

BACKGROUND OF THE INVENTION

1. Field of the Invention

The invention relates to endoscopic scissors. More particularly, the invention relates to an endoscopic scissors having scissor elements and a clevis where the scissor elements are held tightly to each other at their pivot point, but are loosely engaged with the clevis.

2. State of the Art

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera, magnifying lens, or other optical instrument is often inserted through one trocar tube, while a scissors, dissector, or other surgical instrument is inserted through another trocar tube for purposes of manipulating and/or cutting the internal organ. Sometimes it is desirable to have several trocar tubes in place at once in order to receive several surgical instruments. In this manner, organs or tissue may be grasped with one surgical instrument, and simultaneously may be cut with another surgical instrument; all under view of the surgeon.

By 1996, it is expected that more than two million additional endosurgeries will be performed per year that, in 1990, were done via open surgery (MedPRO Month, I:12, p. 178). The advantages of endoscopic surgery are clear in that it is less invasive, less traumatic and recovery is typically quicker. As a result, many new instruments and devices for use in endosurgery are introduced every year.

Endoscopic surgical instruments generally include a tube, a push rod which extends through the tube, an actuating means engaging the tube and the push rod for imparting reciprocal axial motion to the push rod, end effector means coupled to the push rod by linkage means, and a clevis coupled to the tube at its proximal end and to the end effector means at its distal end, wherein axial movement of the push rod effects movement of the end effector means in a plane parallel to the longitudinal axis of the push rod. For purposes herein, the "distal end" of a surgical instrument or any part thereof, is the end most distant from the surgeon and closest to the surgical site, while the "proximal end" of the instrument or any part thereof, is the end most proximate the surgeon and farthest from the surgical site.

End effectors for endoscopic surgical instruments take many forms and scissors are common among them. Endoscopic scissors, like all scissors, include a pair of scissor elements (blades) attached to the clevis by a threaded pivot axle. Endoscopic scissors may be single acting or double acting. In a single acting endoscopic scissors, a first scissor element is held stationary relative to the clevis and a second scissor element is rotated about the pivot axle relative to the first scissor element. As one or both of the scissor elements are rotated relative to each other about the axle, a moving point of contact between the cutting edges of the scissor elements effects cutting of an object in its path. In endoscopic scissors, as with any kind of scissors it is important to keep the cutting edges tightly pressed against each other at their moving point of contact. It has been known generally in the art of scissors to hold the cutting edges of the scissor elements tightly together by tightening a threaded pivot axle via a screwing action. With endoscopic scissors, however, tightening the threaded pivot axle has an unwanted side effect. Since the pivot axle on which endoscopic scissors rotate is coupled to the clevis, tightening the axle to press the scissor elements together also presses the arms of the clevis together. This results in large frictional forces being generated between the scissor elements and the clevis, thereby making operation of the endoscopic scissors difficult.

SUMMARY OF THE INVENTION

It is therefore an object of the invention to provide an endoscopic scissors where the scissor blades act tightly against each other but are not subjected to large frictional forces of the clevis.

It is another object of the invention to provide a means for tightly pressing endoscopic scissor elements together without pressing the arms of the clevis together.

It is also an object of the invention to provide a clevis and a pivot axle which hold double acting scissor elements tightly together but which maintain the scissor elements in a relatively loose engagement with the clevis.

It is a further object of the invention to provide a single acting endoscopic scissors where the rotating scissor element is held in tight relationship with the non-rotating scissor element but in loose relationship with the clevis.

In accord with these objects which will be discussed in detail below, the endoscopic scissors of the present invention include a clevis having a non-threaded relatively large diameter bore in its first arm and relatively smaller diameter bore in its second arm. In a single acting embodiment of the invention, the smaller diameter bore in the second arm of the clevis is threaded. A pair of scissor elements having mounting/pivot holes are mounted between the clevis arms with an axle pin having a threaded end and a larger diameter cylindrical screw head. The scissor elements are positioned between the arms of the clevis so that the stationary scissor element abuts the second arm of the clevis and the mounting/pivot holes of both scissor elements align with the smaller diameter threaded bore in the second arm of the clevis. The axle pin is inserted with its threaded end entering the larger diameter bore of the first clevis arm. The threaded end of the axle pin passes through the mounting/pivot holes in the scissor elements and threadably engages the threaded bore in the second arm of the clevis. The larger diameter screw head is turned with a screwdriver and passes freely into the larger diameter throughbore of the first clevis arm.

The axle pin is tightened with the screwdriver until its larger diameter screw head presses firmly against the scissor elements clamping them firmly against each other and the second arm of the clevis without pressing the clevis arms together.

In a double acting embodiment of the invention, the smaller diameter bore on the second arm of the clevis is non-threaded and the mounting/pivot hole of one of the scissor elements is threaded. The scissor elements are mounted between the clevis arms with an axle pin having a threaded middle portion, a relatively small diameter non-threaded end and a relatively larger diameter cylindrical screw head. The scissor elements are positioned between the arms of the clevis so that the scissor element having the threaded mounting/pivot hole abuts the second arm of the clevis and the mounting/pivot holes of both scissor elements align with the smaller diameter non-threaded bore in the second arm of the clevis. The axle pin is inserted with its non-threaded end entering the larger diameter bore of the first clevis arm. The non-threaded end of the axle pin passes through the mounting/pivot holes in the scissor elements and into the non-threaded bore in the second arm of the clevis while the threaded middle portion of the axle pin engages the threaded mounting/pivot hole in the scissor element adjacent the second clevis arm. The larger diameter cylindrical screw head is turned with a screwdriver and passes freely into the larger diameter bore of the first clevis arm. The axle pin is tightened with the screwdriver until its larger diameter cylindrical screw head presses firmly against the scissor element adjacent the first clevis arm clamping the scissor elements against each other while maintaining loose engagement with the clevis.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
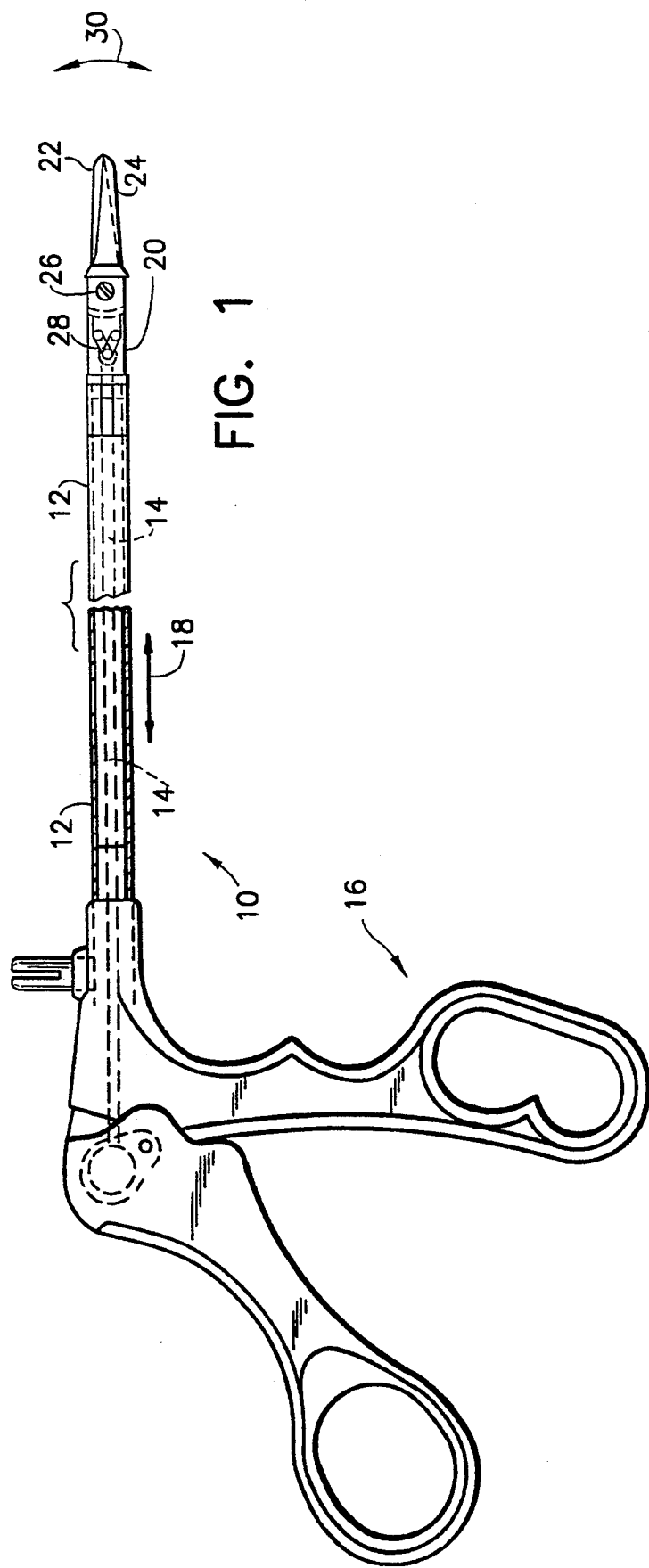
FIG. 1 is a side elevation view in partial section of an endoscopic scissors instrument according to the invention.

Turning now to FIG. 1, the endoscopic scissors 10 according to the invention generally comprises a tube 12, a push rod 14 which extends through the tube 12, an actuating means 16 engaging the tube 12 and the push rod 14 at their proximal ends for imparting reciprocal axial motion to the push rod 14 as shown by arrows 18. A clevis 20 is coupled to the distal end of the tube 12 and a pair of scissor elements 22, 24, are mounted on the clevis 20 by means of an axle pin 26. At least one of the scissor elements 22, 24 is coupled to the push rod 14 by linkage means 28 so that axial movement of the push rod effects rotational movement of at least one of the scissor elements 22, 24 as shown by the arrows 30.

A first embodiment of the invention is shown in greater detail in FIGS. 2, 4, 4a, 6, 6a, and 6b. While the scissors shown in these Figures are curved scissors, the invention is applicable to straight and hooked scissors as well. As seen in these Figures, it will be appreciated that the clevis 20 is a generally cylindrical member having a U-shaped cut-out distal portion defining two arms 20a, 20b. The proximal end 20c of the clevis 20 which is preferably faceted or knurled is either force fit or otherwise inserted into the distal end of tube 12 which may be crimped thereon. A longitudinal axial bore 20d allows the passage of the push rod 14 into the clevis between the two clevis arms 20a, 20b. The distal end of the push rod 14 which enters between arms 20a, 20b of the clevis 20 is provided with a flattened portion 14a for coupling with a linkage 28. The linkage 28 can take any of various forms such as disclosed in co-owned U.S. Pat. Nos. 5,192,298, 5,171,258. The first clevis arm 20a is provided with a relatively large diameter non-threaded bore 20e and the second clevis arm 20b is provided with a relatively small diameter threaded bore 20f for receiving the axle pin 26. According to the preferred embodiment of the single acting instrument, the second clevis arm 20b is also provided with a second bore 20g for receiving a projection of the stationary scissor element 22 as discussed in more detail below.

Figure 2:
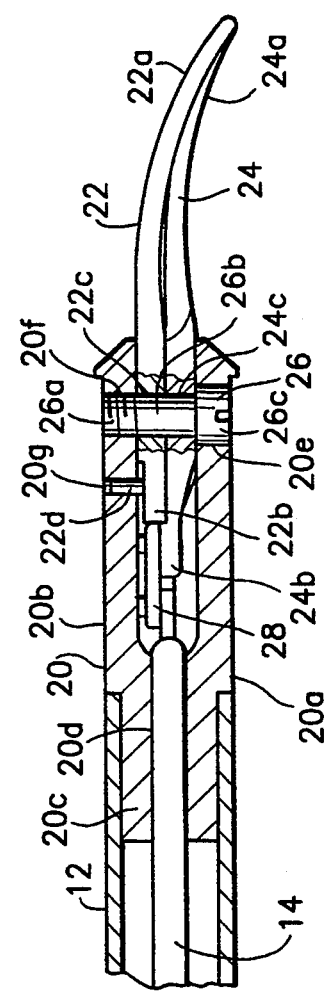
FIG. 2 is an enlarged top view in partial section of the clevis assembly of a single acting embodiment of the invention.

The stationary scissor element 22 has a distal cutting portion 22a, a proximal mounting portion 22b, and an axle pin receiving hole 22c therebetween. The mounting portion 22b is provided with a lateral projection 22d which fits into the second bore 20g of the second clevis arm 20b as seen best in FIG. 2, thereby holding the scissor element 22 stationary relative to the clevis 20. The rotating scissor element 24 is provided with a distal cutting portion 24a, a proximal tang 24b, and an axle pin receiving hole 24c. The proximal tang 24b is provided with a hole 24d for receiving a pin 25a which couples the tang 24b with the linkage 28 as seen best in FIGS. 2, 4, and 4a. The stationary scissor element 22 is placed between the clevis arms 20a, 20b so that its lateral projection enters second bore 20g of clevis arm 20a and its axle pin receiving hole 22c is aligned with the threaded bore 20f in the clevis arm 20a. The rotating scissor element 24 is placed between clevis arm 20a and the scissor element 22 so that its axle pin receiving hole 24c is aligned with the axle pin receiving hole 22c of the stationary scissor element 22 and its tang 24b couples with linkage 28. The axle pin 26 is inserted into the axle pin receiving holes 22c, 24c of the scissor elements 22, 24 as seen in FIG. 2.

In this first embodiment, the axle pin 26 (seen best in FIGS. 2 and 6b) is provided with a threaded small diameter end 26a, a non-threaded middle 26b and a larger diameter cylindrical screw head 26c. The threaded end 26a of axle pin 26 is screwed into the threaded bore 20f of clevis arm 20b. The cylindrical screw head 26c passes freely into the non-threaded larger bore 20e of clevis arm 20a and presses tightly against scissor element 24 because the axle pin receiving hole 24c in scissor element 24 has a smaller diameter than the diameter of the cylindrical screw head 26c. Those skilled in the art will appreciate that the two scissor elements are thereby pressed tightly against each other and held tightly against the second clevis arm 20b while the first clevis arm 20a is not pressed by the axle pin 26 against the rotating scissor element 24.

Figure 4:
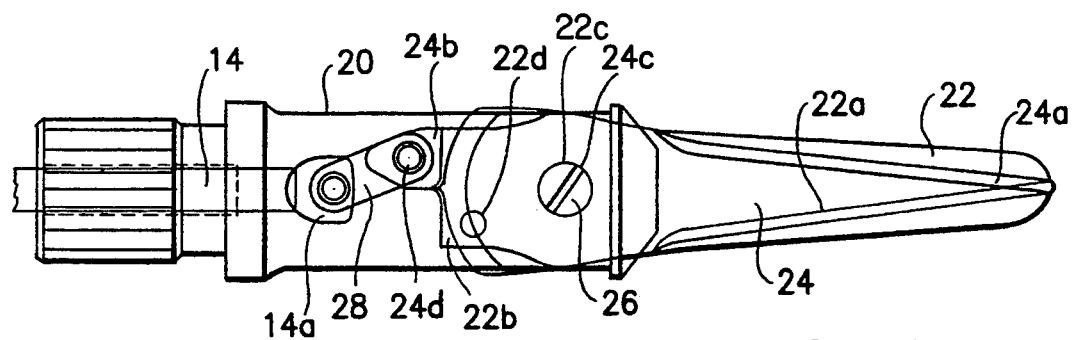
FIG. 4 is an enlarged transparent side view of the embodiment of FIG. 2 in the closed position.
Figure 4A:
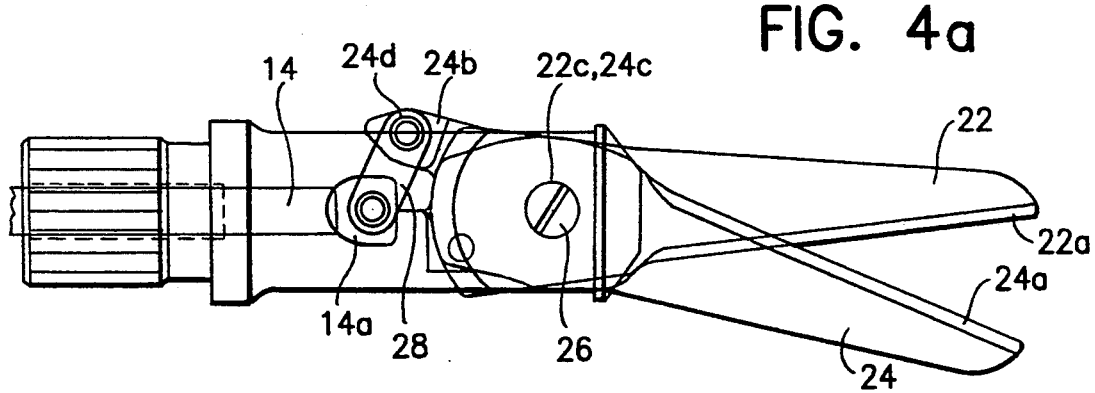
FIG. 4a is an enlarged transparent side view of the embodiment of FIG. 2 in the opened position.

As shown in FIGS. 4 and 4a, movement of the push rod 14 effects a rotational movement of scissor element 24 while the scissor element 22 is held stationary. From these Figures and the description given above, it will be appreciated that the scissor elements can be held tightly together by the axle pin 26 without inducing any friction relative to the clevis when the scissors are operated. In other words, the only frictional engagement effected by tightening the axle pin 26 is the frictional engagement between the scissor elements 22, 24. This is in part due to the fact that scissor element 22 is held stationary, and in part due to the fact that the axle pin 26 floats freely in clevis arm 20a.

This first embodiment of the invention works particularly well in a single acting scissors as described above. While it can certainly be used with some advantage in a double acting scissors, the second embodiment of the invention, which is described below is the preferred embodiment for use with double acting scissors.

The second embodiment of the invention is shown in greater detail in FIGS. 3, 5, 5a, and 6c. In the second embodiment, the clevis 120 is similar to the clevis 20 and as will be described below, clevis 20 could be used in this embodiment depending on the dimensions of the axle pin 126. Clevis 120 has a U-shaped cut-out distal portion defining two arms 120a, 120b. A faceted or knurled proximal end 120c is press fit or otherwise inserted into the distal end of tube 12 which may be crimped thereon. A longitudinal axial bore 120d allows the passage of the push rod 14 into the clevis between the two clevis arms 120a, 120b. The distal end of the push rod 14 which enters between arms 120a, 120b of the clevis 120 is provided with a flattened portion 14a for coupling with linkages 28a, 28b. In this second embodiment, the scissors are double acting, i.e., both scissor elements 122, 24 are rotatable about the axle pin 126. Therefore, there is no need to hold either of the scissor elements stationary. The first clevis arm 120a is provided with a relatively large diameter non-threaded bore 120e and the second clevis arm 120b is provided with a relatively small diameter non-threaded bore 120f for receiving the axle pin 126.

Scissor element 122 has a distal cutting portion 122a, a proximal tang 122b, and a threaded axle pin receiving hole 122c therebetween. Proximal tang 122b is provided with a hole 122d for receiving a pin 25a which couples the tang 122b with the linkage 28b as seen best in FIGS. 5 and 5a. Scissor element 24 is identical to scissor element 24 described above and is coupled at its tang 24b to linkage 28a by pin 25b. Scissor elements 122 and 24 are placed between the clevis arms 120a, 120b so that their axle pin receiving holes 122c, 24c are aligned with the non-threaded bore 120f in the clevis arm 120a and their tangs 122b, 24b couple with the linkages 28b, 28a.

Figure 3:
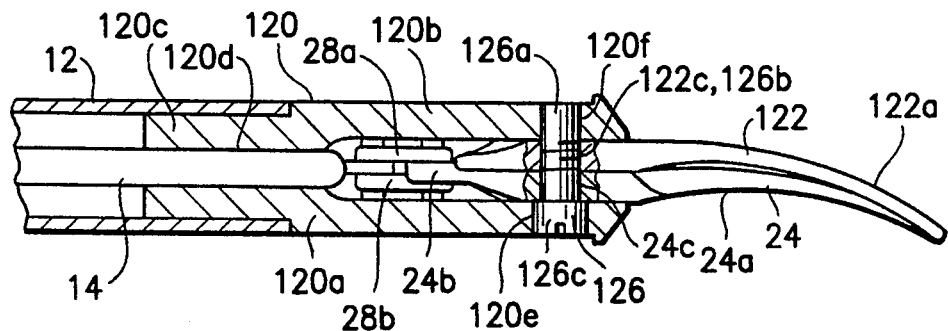
FIG. 3 is a view similar to FIG. 3, but of a double acting embodiment of the invention.

Axle pin 126 is inserted into the axle pin receiving holes 122c, 24c of the scissor elements 122, 24 as seen in FIG. 3.

In this second (double acting) embodiment, axle pin 126 (seen best in FIGS. 3 and 6c) is provided with a non-threaded small diameter end 126a, a threaded middle 126b and a larger diameter cylindrical screw head 126c. The non-threaded end 126a of axle pin 126 enters into the non-threaded bore 120f of the clevis arm 120b as the threaded middle 126b engages the threaded axle pin receiving hole 122c of the scissor element 122. The cylindrical screw head 126c passes freely into the non-threaded larger bore 120e of the clevis arm 120a and presses tightly against scissor element 24 because the axle pin receiving hole 24c in scissor element 24 has a smaller diameter than the diameter of the cylindrical screw head 126c. Those skilled in the art will appreciate that the two scissor elements are thereby pressed tightly against each other but not against either clevis arm 120a, 120b. The axle pin 126 floats in the bores 120e, 120f of the clevis 120.

Figure 5:
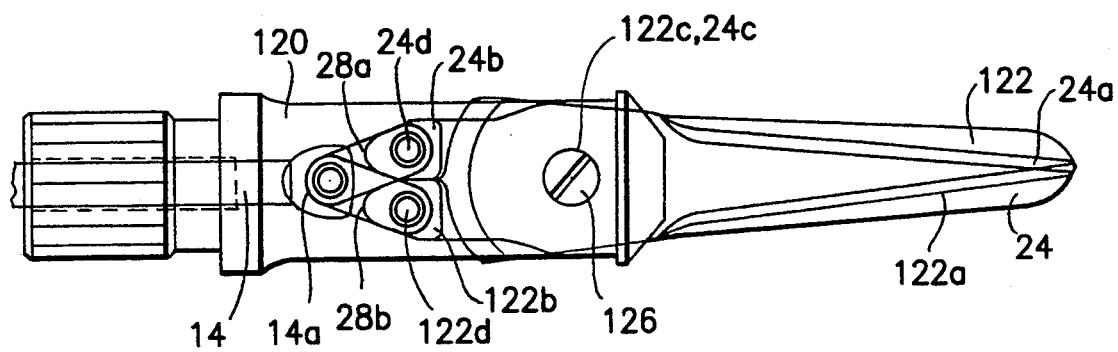
FIG. 5 is an enlarged transparent side view of the embodiment of FIG. 3 in the closed position.
Figure 5A:
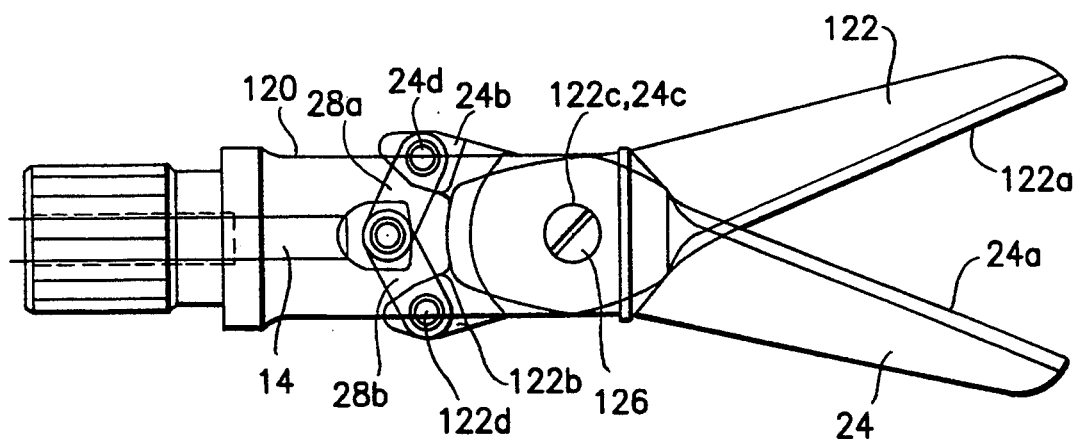
FIG. 5a is an enlarged transparent side view of the embodiment of FIG. 3 in the opened position.
Figure 6:
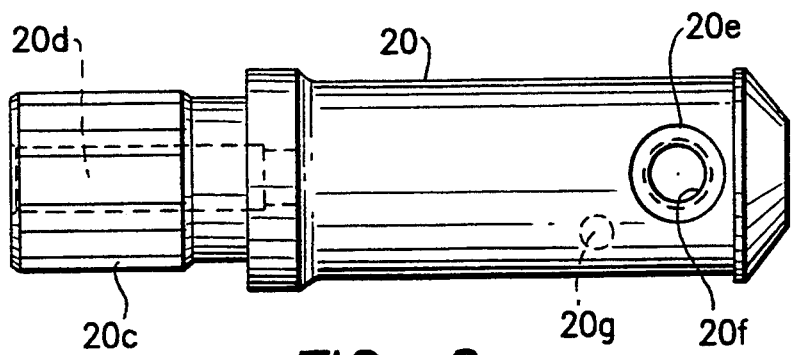
FIG. 6 is an enlarged side view of the clevis of FIGS. 2 and 4.
Figure 6A:
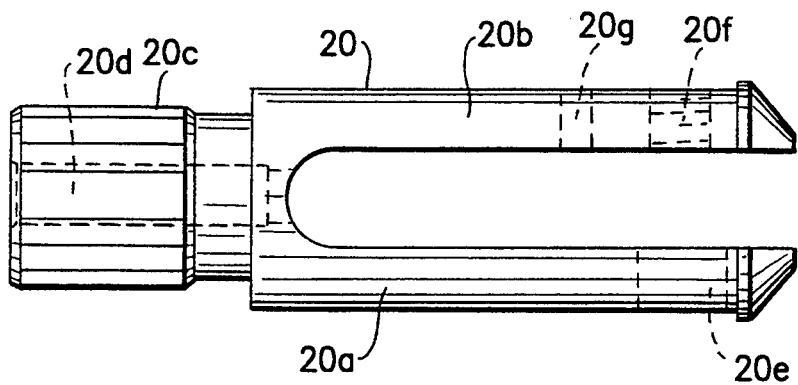
FIG. 6a is an enlarged top view of the clevis of FIGS. 2 and 4.
Figure 6B:
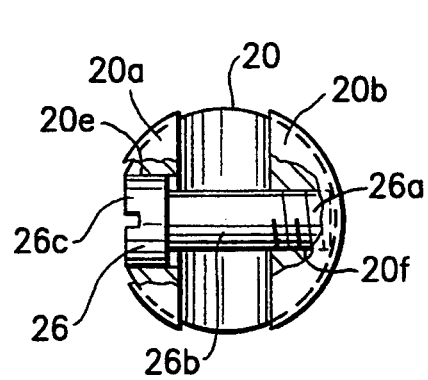
FIG. 6b is an enlarged distal end view of the clevis and axle pin of FIGS. 2 and 4.
Figure 6C:
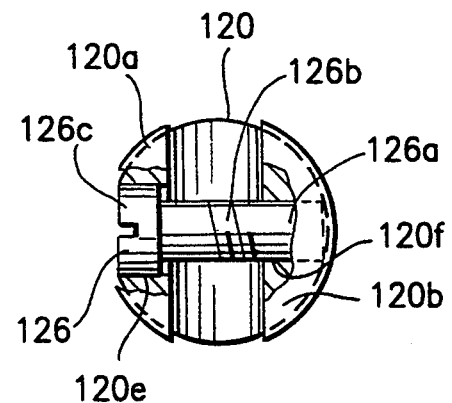
FIG. 6c is a view similar to FIG. 6b but of the clevis and axle pin of FIGS. 3 and 5.

As shown in FIGS. 5 and 5a, movement of the push rod 14 effects a rotational movement of both scissor elements 24 and 122. From FIGS. 5 and 5a and the description given above, it will be appreciated that the scissor elements are held tightly together by the axle pin 126 without inducing any friction relative to the clevis when the scissors are operated. In other words, the only frictional engagement effected by the tightening of the axle pin 126 is the frictional engagement between the scissor elements 122 and 24. This is due to the fact that scissor element 122 is threadably engaged by the threaded middle portion 126b of axle pin 126 while the non-threaded ends 126a, 126c of the axle pin 126 float freely in the clevis arms 120a, 120b.

This second embodiment of the invention works particularly well in a double acting scissors as described above. Nevertheless, those skilled in the art will appreciate that this embodiment could be used with single acting scissors provided that one of the scissor elements is held stationary. Moreover, so long as the non-threaded end 126a of the axle pin 126 has a small enough diameter, it does not matter whether or not the bore 120f (20f) in clevis arm 120b (20b) is threaded. Similarly, it will be appreciated that so long as the threaded hole 122c in scissor element 122 is properly dimensioned, scissor element 122 can be used in either the first or second embodiments described above.

Figure 7:
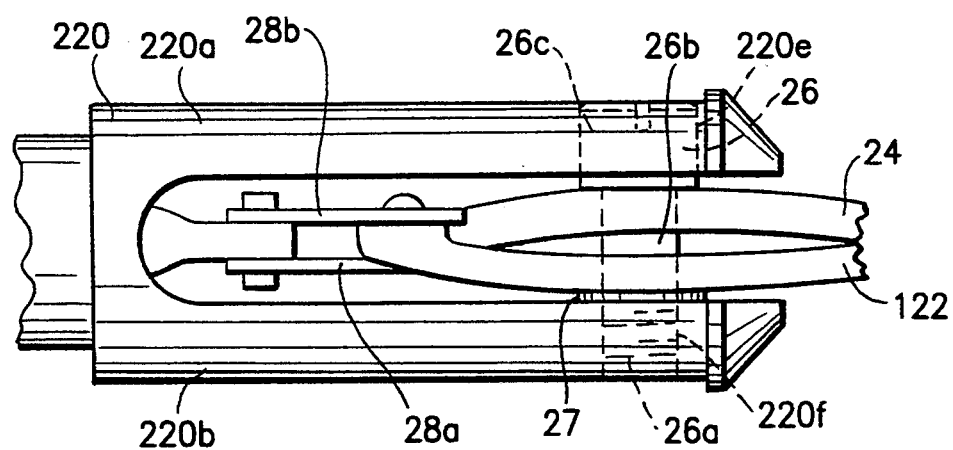
FIG. 7 is a fragmented bottom view of the presently preferred double acting embodiment of the invention.

FIG. 7 is an enlarged segmented view similar to FIG. 3 of an alternate double acting embodiment of the invention. Here clevis arm 220a of clevis 220 is provided with a relatively large diameter non-threaded bore 220e and clevis arm 220b is provided with a relatively small diameter threaded bore 220f. This arrangement is similar to clevis 20 in the single acting embodiment of FIG. 2, but without the second bore in the second clevis arm. Axle pin 26 is used in this embodiment with the addition of a washer 27. Those skilled in the art will appreciate that this embodiment is similar to the single acting embodiment but with the addition of the washer. The washer 27, which is preferably stainless steel, aids in centering the double acting scissor elements 24, 122 between the clevis arms 220a, 220b and reduces friction and wear between scissor element 122 and clevis arm 220b. If desired, instead of a stainless steel washer, the washer may be made from a non-reactive lubricious plastic material. Alternatively, the stainless steel washer may be coated with a lubricant.

There have been described and illustrated herein several embodiments of an endoscopic scissors having scissor elements loosely engaged with the clevis. While particular embodiments of the invention have been described, it is not intended that the invention be limited thereto, as it is intended that the invention be as broad in scope as the art will allow and that the specification be read likewise. Thus, while particular clevis designs have been disclosed, it will be appreciated that other clevis designs could be utilized so long as the axle pin is held in a position allowing rotation of one or both of the scissor elements. Also, while curved scissors have been shown, it will be recognized that other types of scissors could be used with similar results obtained. Moreover, while particular configurations have been disclosed in reference to the axle pin, it will be appreciated that other configurations could be used as well so long as the axle pin does not press the two arms of the clevis together. Furthermore, while the axle pin has been disclosed as having screw head, it will be understood that different types of heads can achieve the same or similar function as disclosed herein. It will therefore be appreciated by those skilled in the art that yet other modifications could be made to the provided invention without deviating from its spirit and scope as so claimed.

We claim:

1. An endoscopic scissors, comprising:
   a) a hollow tube having a proximal end and a distal end;
   b) a push rod extending through said hollow tube, said push rod having a proximal end and a distal end;
   c) actuation means coupled to said proximal end of said tube and said proximal end of said push rod for imparting reciprocal axial motion to said push rod within said tube;
   d) a clevis coupled to said distal end of said tube, said clevis having a first clevis arm and a second clevis arm, said first clevis arm having a first bore of a first diameter and said second clevis arm having a second bore of a second diameter, said second diameter being smaller than said first diameter, said distal end of said push rod extending into said clevis between said first and second clevis arms;
   e) first and second scissor elements, each scissor element having a hole, at least one of said first and second scissor elements being coupled to said push rod; and
   f) an axle pin having a smaller diameter portion and a larger diameter portion, said axle pin extending through the holes in said scissor elements with said smaller diameter portion of said axle pin entering said second bore in said second clevis arm and said larger diameter portion of said axle pin entering said first bore in said first clevis arm,
   wherein said axle pin is provided with a threaded portion engaging one of said second bore in said second clevis arm and said hole in said second scissor element, said axle pin pressing said scissor elements close to each other without pressing said first and second clevis arms close to each other.

2. An endoscopic scissors according to claim 1, wherein:
   said second bore in said second clevis arm is threaded and is engaged by said threaded portion of said axle pin.

3. An endoscopic scissors according to claim 1, wherein:
   said hole in said second scissor element is threaded and is engaged by said threaded portion of said axle pin.

4. An endoscopic scissors according to claim 2, wherein:
   said threaded portion of said axle pin is an end part of said smaller diameter portion of said axle pin.

5. An endoscopic scissors according to claim 3, wherein:
   said threaded portion of said axle pin is a middle part of said smaller diameter portion of said axle pin.

6. An endoscopic scissors according to claim 1, wherein:
   said larger diameter portion of said axle pin floats in said first bore in said first clevis arm.

7. An endoscopic scissors according to claim 6, wherein:
   said smaller diameter portion of said axle pin floats in said second bore in said second clevis arm.

8. An endoscopic scissors according to claim 1, further comprising:
   g) washer means for extending around said axle pin and located between said second clevis arm and said second scissor element.

9. An endoscopic scissors according to claim 8, wherein:
   said second bore in said second clevis arm is threaded and is engaged by said threaded portion of said axle pin.

10. An endoscopic scissors according to claim 9, wherein:
    said washer means is a stainless steel washer.

11. An endoscopic scissors according to claim 1, wherein:
    only one of said first and second scissor elements is coupled to said push rod,
    the other of said first and second scissor elements being provided with a lateral projection, and
    a respective one of said first and second clevis arms is provided with a third bore receiving said lateral projection and thereby holds said other of said first and second scissor elements stationary against rotation.

12. A clevis apparatus for use in an endoscopic instrument having a first and second end effector, each end effector having a hole for mounting the end effectors in the clevis apparatus, said clevis apparatus comprising:
    a) a first clevis arm having a first bore of a first diameter;
    b) a second clevis arm having a second bore of a second diameter, said second diameter being smaller than said first diameter;
    c) an axle pin having a smaller diameter portion and a larger diameter portion, said axle pin extending through the holes in the end effectors with said smaller diameter portion of said axle pin entering said second bore in said second clevis arm and said larger portion of said axle pin entering said first bore in said first clevis arm,
    wherein said axle pin is provided with a threaded portion engaging one of said second bore in said second clevis arm and the hole in the second end effector, said axle pin pressing the end effectors close to each other without pressing said clevis arms close to each other.

13. A clevis apparatus according to claim 12, where the second end effector has a lateral projection, wherein:

said second clevis arm is provided with a third bore receiving the lateral projection on the second end effector to hold the second end effector stationary against rotation.

14. A clevis apparatus according to claim 12, further comprising:

d) washer disposed on said axle pin between said second clevis arm and the second end effector.

15. A clevis apparatus according to claim 14, wherein:

said relatively small diameter bore is threaded and said threaded portion of said axle pin engages said second bore.

16. A clevis apparatus according to claim 13, wherein:

said relatively small diameter bore is threaded and said threaded portion of said axle pin engages said second bore.

17. A clevis apparatus according to claim 12 where the hole in the second end effector is a threaded hole, wherein:

said threaded portion of said axle pin engages the threaded hole in the second end effector.

* * * * *